(12) United States Patent
Saitoh

(10) Patent No.: US 8,609,869 B2
(45) Date of Patent: Dec. 17, 2013

(54) HETEROAROMATIC-CONTAINING COMPOUND, OPTICAL MATERIAL AND OPTICAL ELEMENT

(75) Inventor: Terunobu Saitoh, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/501,012

(22) PCT Filed: Dec. 16, 2010

(86) PCT No.: PCT/JP2010/073258
§ 371 (c)(1),
(2), (4) Date: Apr. 9, 2012

(87) PCT Pub. No.: WO2011/081078
PCT Pub. Date: Jul. 7, 2011

(65) Prior Publication Data
US 2012/0203012 A1    Aug. 9, 2012

(30) Foreign Application Priority Data

Dec. 28, 2009  (JP) ................................ 2009-298642

(51) Int. Cl.
*C07D 333/02*   (2006.01)
(52) U.S. Cl.
USPC ........................................................... 549/29
(58) Field of Classification Search
USPC ............................................. 549/59, 70, 72
See application file for complete search history.

(56) References Cited

U.S. PATENT DOCUMENTS

| | | | |
|---|---|---|---|
| 5,290,952 A * | 3/1994 | Leppard et al. ................. | 549/72 |
| 6,034,275 A | 3/2000 | Aebi et al. | |
| 6,441,177 B1 | 8/2002 | Aebi et al. | |

FOREIGN PATENT DOCUMENTS

| | | | |
|---|---|---|---|
| EP | 0 521 823 A1 | | 1/1993 |
| EP | 0 778 264 A1 | | 6/1997 |
| GB | 973919 | * | 11/1964 |
| GB | 2146647 A | | 4/1985 |
| JP | 2008-158361 A | | 7/2008 |

OTHER PUBLICATIONS

Chiacchio, U., et al. "The Reaction of Unsaturated Carbonyl Compounds with 'Activated' Sulfur (II). Formation of Cyclic Disulfide and Polysulfides." Heterocycles. vol. 48, No. 1 (1998), pp. 41-51.*

Furstner, A., et al. "A Convenient Preparation of Functionalized Arylzinc Compounds by the Reaction of Zinc/Silver-Graphite with Aryl Iodides." Tetrahedron Letters. vol. 35, No. 7 (1994), pp. 1047-1050.*

J. C. Meslin Et Al., "Enchainements Heteroatomiques Et Leurs Produits De Cyclisation—I : Vinylogues De Thioamides Comme Intermediaires De Synthese D'acyl-2 Thiophenes, Thio-1 Pyrannones-2 (Thiones), Dihydro-5,6 Dithiinnes-1,2 Dioxydes-1,1 Et Dithiinnes-1,2 Dioxydes-1,1 Substitues," 31(21) Tetrahedron 2679-2684 (1975) (XP002629578).

Si Yan Liao et al., "Binding Orientations, QSAR, and Molecular Design of Thiophene Derivative Inhibitors," 74(3) Chem. Biol. Drug Des. 289-296 (2009) (XP002629579).

Alois Fürstner et al., "A Convenient Preparation of Functionalized Arylzinc Compounds by the Reaction of Zinc/Silver-Graphite with Aryl Iodides," 35(7) Tetrahedron Letters 1047-1050 (1994) (XP002629580).

Ng Ph Buu-Hoi et al., "Thiophene series. VI. The chemistry of 2-p-tolylthiophene and 2-(p-chlorophenyl)thiophene," 69 RECUEIL 1455-1470 (1950) (XP009128377).

Robert T. LaLonde et al., "Variable Reaction Pathways for the Action of Polysulfide on Michael Acceptors," 50(1) J. Org. Chem. 85-91 (1985) (XP002629581).

Alexander Oster et al., "Bicyclic Substituted Hydroxyphenylmethanones as Novel Inhibitors of 17β-Hydroxysteroid Dehydrogenase Type 1 (17β-HSD1) for the Treatment of Estrogen-Dependent Diseases," 53(22) J. Med. Chem. 8176-8186 (Oct. 2010) (XP002629582).

First Office Action in Chinese Application No. 201080058935.5 (dated Apr. 15, 2013).

* cited by examiner

*Primary Examiner* — Noble Jarrell
*Assistant Examiner* — John S Kenyon
(74) *Attorney, Agent, or Firm* — Fitzpatrick, Cella, Harper & Scinto

(57) ABSTRACT

There are provided a heteroaromatic-containing compound represented by the following general formula (1), and an optical material including the heteroaromatic-containing compound.

Formula 1

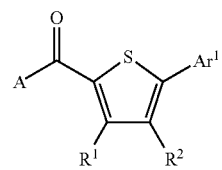

General Formula (1)

wherein $R^1$ and $R^2$ are each independently a hydrogen atom or a methyl group, $Ar^1$ is an aryl group which may have a substituent, and A is an aromatic hydrocarbon group. The $R^1$ and $R^2$ can be a hydrogen atom, and $Ar^1$ can be a phenyl group.

8 Claims, 1 Drawing Sheet

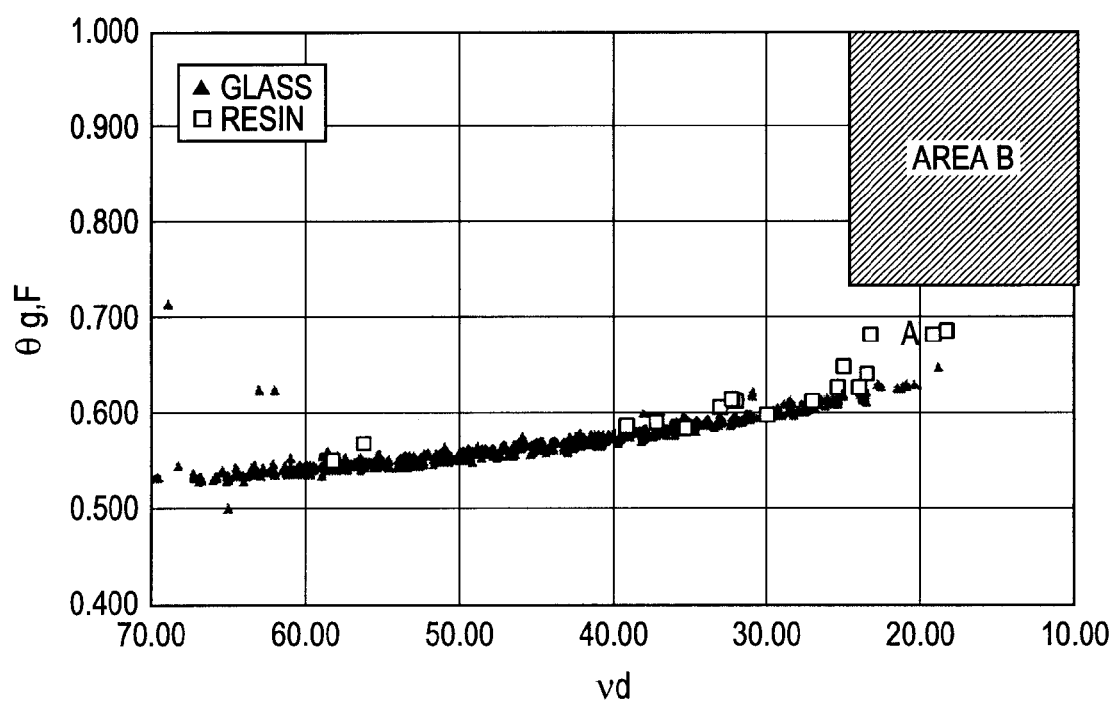

HETEROAROMATIC-CONTAINING COMPOUND, OPTICAL MATERIAL AND OPTICAL ELEMENT

TECHNICAL FIELD

The present invention relates to a heteroaromatic-containing compound, an optical material and an optical element, and particularly to a heteroaromatic-containing compound, an optical material and an optical element which have a low dispersion characteristic of refractive index (Abbe number (vd)) and a high secondary dispersion characteristic (θg, F).

BACKGROUND ART

Refractive indices of optical materials of glass materials, organic resins and the like generally become gradually higher with shorter wavelengths. Indices indicating wavelength dispersions of the refractive indices include Abbe number (vd) and the secondary dispersion characteristic (θg, F). The Abbe number (vd) and secondary dispersion characteristic (θg, F) are values unique to an optical material, but fall into certain ranges in many cases. Refractive indices and Abbe number (vd) of conventional optical materials are shown in FIG. 1.

The Abbe number (vd) and the secondary dispersion characteristic (θg, F) are represented by the following expressions.

$$\text{Abbe number}[vd] = (nd-1)/(nF-nC)$$

$$\text{Secondary dispersion characteristic}[\theta g, F] = (ng-nF)/(nF-nC)$$

wherein nd is a refractive index at a wavelength of 587.6 nm; nF is a refractive index at a wavelength of 486.1 nm; nC is a refractive index at a wavelength of 656.3 nm; and ng is a refractive index at a wavelength of 435.8 nm.

However, by in detail designing constitutions (material types and molecular structures) of optical materials (glass materials, organic resins and the like), optical materials having a high secondary dispersion characteristic (θg, F) apart from the above-mentioned certain range are synthesized. For example, a polyvinylcarbazole as an organic resin (A in FIG. 1) of which secondary dispersion characteristic (θg, F) is higher than general-purpose organic resin materials.

In refractive optical systems, the chromatic aberration is generally reduced by combining glass materials having different dispersion characteristics. For example, in objective lenses of telescopes and the like, a glass material having a small dispersion is used as a plus lens, and a glass material having a large dispersion is used as a minus lens; and by combining these, the chromatic aberration appearing on the axis is corrected. Therefore, in the case where constitutions and the number of lenses are limited, in the case where a glass material to be used is limited, and in other cases, it is sometimes very difficult to sufficiently correct the chromatic aberration. As one method of solving such a problem, there is carried out designing of optical elements by utilizing glass materials having anomalous dispersion characteristics.

In the case of producing optical elements having an aspherical shape or the like excellent in the chromatic aberration correction function, the formation of an organic resin on a spherical glass or the like has better advantages in productivity, moldability, versatility in shape and weight reduction than the use of a glass material as a material. However, optical characteristics of conventional organic resins fall into certain limited ranges as illustrated in FIG. 1, and there are thus very few organic resins exhibiting specific dispersion characteristics.

Japanese Patent Application Laid-Open No. 2008-158361 describes an optical resin composition in which N-acryloylcarbazole, a polyfunctional polyester acylate, dimethyloltricyclodecane diacrylate, and a polymerization initiator are mixed in predetermined ratios. It describes that the optical resin composition is a material which is easily processed and whose cured product has sufficient anomalous dispersion and durability.

On the other hand, the present inventor has paid attention to that, in order to impart a higher chromatic aberration correction function to optical elements than conventionally, material with higher secondary dispersion characteristic (θg, F) is very effective on optical designing. Specifically, in FIG. 1, the characteristic is one within a range B (vd<25 and θg, F>0.73) where the relation between vd and θg, F is apart from plots of glass materials or general-purpose materials of organic resins.

However, there now exists no material having secondary dispersion characteristic (θg, F) within the range B in FIG. 1 and exhibiting little coloration and capable of being stably produced. The materials described in Japanese Patent Application Laid-Open No. 2008-158361 all have a θg, F value of 0.70 or lower.

CITATION LIST

Patent Literature

PTL 1: Japanese Patent Application Laid-Open No. 2008-158361

SUMMARY OF INVENTION

The present invention provides, in consideration of such a background art, a heteroaromatic-containing compound having a low dispersion characteristic of refractive index (Abbe number (vd)), a high secondary dispersion characteristic (θg, F) and a high characteristic of the chromatic aberration correction function, and an optical material and an optical element using the same.

A heteroaromatic-containing compound to solve the above-mentioned problem includes a compound represented by the following general formula (1).

Formula 1

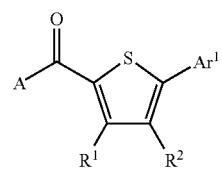

General Formula (1)

(In the formula, $R^1$ and $R^2$ are each independently a hydrogen atom or a methyl group; $Ar^1$ is an aryl group which may have a substituent; and A is an aromatic hydrocarbon group.)

An optical material to solve the above-mentioned problem is an optical material including the heteroaromatic-containing compound described above. An optical element to solve the above-mentioned problem is also an optical element prepared by molding the optical material described above. Further features of the present invention will become apparent from the following description of exemplary embodiments with reference to the attached drawings.

BRIEF DESCRIPTION OF DRAWINGS

FIG. 1 is a graph illustrating relations between the secondary dispersion characteristic (θg, F) and the Abbe number (vd) of commercially available optical materials.

DESCRIPTION OF EMBODIMENTS

Hereinafter, the present invention will be described in detail.

The heteroaromatic-containing compound according to the present invention includes a compound represented by the following general formula (1).

Formula 2

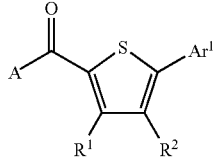

General Formula (1)

(In the formula, $R^1$ and $R^2$ are each independently a hydrogen atom or a methyl group; $Ar^1$ is an aryl group which may have a substituent; and A is an aromatic hydrocarbon group.)

As a result of exhaustive studies on materials satisfying characteristics within the range B in FIG. 1, the present inventor has found that a compound having a reasonably long conjugate structure having many π electrons has a low dispersion characteristic of refractive index (Abbe number (vd)) and a high secondary dispersion characteristic (θg, F). The present inventor has also found that the compound has a high transmittance and is a material optically stable and highly useful. That is, the compound is a heteroaromatic-containing compound in which at least one heterocyclic compound having π electrons is bonded to an aromatic compound through an sp2 carbon atom. In the present invention, the π electrons mean electrons forming π bonds. The sp2 carbon atom means carbon having two single bonds and one double bond in a planar structure.

Since a compound having a long conjugate structure having many π electrons, represented by aromatic compounds, generally has a smaller band gap than general-purpose materials, the absorption edge in the ultraviolet region shifts to the visible light region side. Due to this influence, the compound having a long conjugate structure having many π electrons has a high refractive index characteristic. Since the high refractive index characteristic more affects the short wavelength side, a (θg, F) naturally rises and the characteristics of the compound fall into the range B in FIG. 1. However, a material having a high transmittance and being optically stable and highly useful cannot simply be obtained only by having a long conjugate structure having many π electrons. For example, large aromatic compounds (having many π electrons), polyacetylenes, polythiophenes and the like have problems remaining in points of synthesizability, compatibility with other compounds and coloration. In non-aromatic compounds (polyenes and the like) having a long conjugate structure having many π electrons, the electrocyclic reaction, Diels-Alder reaction and the like advance easily at room temperature, very much reducing preservation stability. That is, the above-mentioned compounds having many π electrons and having a reasonably long conjugate structure are desirable.

As means to achieve the above-mentioned reasonably long conjugate structure containing many π electrons, it is suitable that a heterocyclic compound having π electrons is bonded to an aromatic compound through sp2 carbon. That is, due to a steric repulsion between a substituent in the aromatic compound and a substituent on the sp2 carbon atom, the plane of the aromatic compound and the plane of the sp2 carbon atom are naturally distorted from the same plane. Each of the aromatic compound side and the heterocyclic compound side having π electrons containing an sp2 carbon atom has a reasonably long conjugate structure. Hence, a material is made which has a high transmittance, exhibits optical stability and has a high secondary dispersion characteristic (θg, F). Having a reasonably long conjugate structure can also improve the preservation stability against the electrocyclic reaction, Diels-Alder reaction and the like, the compatibility, the coloration and the like. A heteroatom in the heterocyclic compound having π electrons contributes also to improvement in characteristics of the heteroaromatic-containing compound. That is, this is because unshared electron pairs of the heteroatom favorably affect elongation of a conjugate structure having a reasonable length.

The incorporation of a heteroatom improves the preservation stability of the heteroaromatic-containing compound in some cases. For example, cyclopentadiene being a 5-membered cyclic compound (containing no heteroatom) having π electrons has a very high reactivity and always exists only as a dimmer at room temperature. By contrast, thiophene, furan, pyrrole and the like being a 5-membered cyclic compound having a similar skeleton and a heteroatom incorporated therein exist stably as not a dimmer but a monomer by aromatization by unshared electron pairs.

For the reason described hitherto, a heteroaromatic-containing compound in which a heterocyclic compound having π electrons is bonded to an aromatic compound through sp2 carbon is suitable as means to solve the above-mentioned problems. This fact is supported also by a simulation result from a discrete Fourier transform.

The heteroaromatic-containing compound represented by the general formula (1) is a heteroaromatic-containing compound in which an aromatic hydrocarbon group A and a heterocyclic group including a heterocyclic compound are bonded through a carbon atom having an oxygen atom double-bonded therewith.

A heterocycle including a heterocyclic compound in the general formula (1) is represented by the following general formula (5).

Formula 3

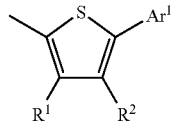

General Formula (5)

$R^1$ and $R^2$ are not especially limited as long as not degrading characteristics of the heteroaromatic-containing compound, and are each independently an alkyl group having 1 to 4 carbon atoms, an aryl group which may have a substituent, a halogen atom, a hydrogen atom or the like. In consideration of the decrease in characteristics, the easiness of synthesis and the like, $R^1$ and $R^2$ can each independently be a hydrogen atom or a methyl group, and can further be a hydrogen atom. The alkyl group having 1 to 4 carbon atoms includes a methyl group, an ethyl group, a vinyl group, a propyl group, a propenyl group, an allyl group, an i-propyl group, a butyl group, an i-butyl group, and a t-butyl group. The aryl group which may have a substituent is a phenyl group, a naphthyl group, an anthracenyl group, 4-methylphenyl group, a 4-methoxyphenyl group, a 4-chlorophenyl group, a 4-fluorophenyl group, a 4-bromophenyl group, a 4-iodophenyl group, a 4-dimethylaminophenyl group, a 2-methylphenyl group, a 2-methoxyphenyl group, a 2-dimethylaminophenyl group, and a 4-nitrophenyl group, and is not limited thereto. The halogen atom includes fluorine, chlorine, bromine, or iodine.

$Ar^1$ is an aryl group which may have a substituent. Having an aryl group makes a reasonably long conjugate structure as compared with a thiophene ring alone, and improves characteristics of the heteroaromatic-containing compound. The aryl group which may have a substituent includes a phenyl group, a naphthyl group, an anthracenyl group, 4-methylphenyl group, a 4-methoxyphenyl group, a 4-chlorophenyl group, a 4-fluorophenyl group, a 4-bromophenyl group, a 4-iodophenyl group, a 4-dimethylaminophenyl group, a 4-vinylphenyl group, a 4-allylphenyl group, a 2-methylphenyl group, a 2-methoxyphenyl group, a 2-dimethylaminophenyl group, a 4-nitrophenyl group, a 2-vinylphenyl group, and a 2-allylphenyl group, and is not limited thereto. The aryl group which may have a substituent can be a phenyl group in consideration of the easiness of synthesis and the characteristics.

The carbon atom having an oxygen atom double-bonded therewith in the general formula (1) is represented by the following general formula (6).

Formula 4

General Formula (6)

The aromatic hydrocarbon group in the general formula (1) is not especially limited as long as being an aromatic compound, and includes ones containing, as a main skeleton, for example, benzene, naphthalene, anthracene, fluorene, biphenyl, diaryl ether, diaryl sulfide, binaphthalene, pyridine, carbazole, thianthrene, dibenzodioxane, benzofuran, acenaphthylene, acridine, benzothiazole, quinoline, isoquinoline, pyrene, indazole, indole, indan, indene, benzoquinoline, benzoxazole, biquinoline, phenanthrene, phenanthroline, bifluorenylidene, ferrocene, phenoxathiin, dibenzothiophene and dibenzofuran. The aromatic hydrocarbon group can be ones containing benzene or naphthalene as a main skeleton in consideration of the easiness of synthesis, the characteristics and the coloration.

The aromatic hydrocarbon group containing naphthalene as a main skeleton desirably has a structure represented by the following general formula (2).

Formula 5

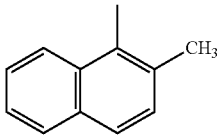

General Formual (2)

The aromatic hydrocarbon group containing benzene as a main skeleton desirably has a structure represented by the following general formula (3).

Formula 6

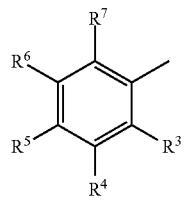

General Formula (3)

(In the formula, $R^3$ to $R^7$ are each independently X, Y, a hydrogen atom, an alkyl group having 1 to 4 carbon atoms, or an aryl group which may have a substituent; X is a second bonding position in the case where two or more of the structures represented by the above general formula (1) are present in a same molecule; and Y is a group including a structure represented by the following general formula (4), or a hydroxyl group:

Formula 7

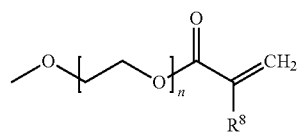

General Formula (4)

$R^8$ is a hydrogen atom or a methyl group; and n is 0 or 1.)

The alkyl group having 1 to 4 carbon atoms includes a methyl group, an ethyl group, a propyl group, an i-propyl group, a butyl group, an i-butyl group, and a t-butyl group.

The aryl group which may have a substituent includes a phenyl group, a naphthyl group, an anthracenyl group, a 4-methylphenyl group, a 4-methoxyphenyl group, a 4-chlorophenyl group, a 4-fluorophenyl group, a 4-bromophenyl group, a 4-iodophenyl group, a 4-dimethylaminophenyl group, a 2-methylphenyl group, a 2-methoxyphenyl group, a 2-dimethylaminophenyl group, and a 4-nitrophenyl group, and is not limited thereto.

Further in consideration of the easiness of synthesis, the characteristics, the coloration or the like, $R^3$ to $R^7$ in the general formula (3) shown above are preferably one combination selected from the combination group consisting of: $R^3$ and $R^7$ are a methyl group, and $R^4$, $R^5$ and $R^6$ are a hydrogen atom; $R^3$, $R^5$ and $R^7$ are a methyl group, and $R^4$ and $R^6$ are a hydrogen atom; $R^3$ is a methyl group, and $R^4$, $R^5$, $R^6$ and $R^7$ are a hydrogen atom; $R^3$, $R^5$ and $R^6$ are a methyl group, and $R^4$ and $R^7$ are a hydrogen atom; $R^3$ and $R^4$ are a methyl group, and $R^5$, $R^6$ and $R^7$ are a hydrogen atom; $R^3$ is an isopropyl group, and $R^4$, $R^5$, $R^6$ and $R^7$ are a hydrogen atom; $R^3$ and $R^5$ are Y, and $R^4$, $R^6$ and $R^7$ are a hydrogen atom; $R^3$ and $R^4$ are Y, and $R^5$, $R^6$ and $R^7$ are a hydrogen atom; $R^3$ is Y, and $R^4$, $R^5$, $R^6$ and $R^7$ are a hydrogen atom; $R^3$ is Y, and $R^4$, $R^5$ and $R^7$ are a hydrogen atom, and $R^6$ is a methyl group; $R^3$ and $R^7$ are a methyl group, and $R^4$ and $R^6$ are a hydrogen atom, and $R^5$ is Y; $R^3$ is Y, and $R^4$ and $R^6$ are a tert-butyl group, and $R^5$ and $R^7$ are a hydrogen atom; $R^3$, $R^5$ and $R^7$ are Y, and $R^4$ and $R^6$ are a hydrogen atom; $R^3$, $R^4$ and $R^5$ are Y, and $R^6$ and $R^7$ are a hydrogen atom; $R^3$ is Y, and $R^4$ is a methyl group, and $R^5$, $R^6$ and $R^7$ are a hydrogen atom; $R^3$ is Y, and $R^4$ is X, and $R^5$, $R^6$ and $R^7$ are a hydrogen atom; and $R^3$ is Y, and $R^4$ is X, and $R^5$ and $R^7$ are a hydrogen atom, and $R^6$ is a methyl group. X is a site to be bonded with the carbon atom described above, and Y is a site to be bonded with the structure represented by the general formula (4), or a hydroxyl group.

In consideration of the easiness of synthesis, the characteristics, the coloration or the like, X in the general formula (3) can further be sites to be bonded with the sp2 carbon atoms described above, and can be one combination selected from the combination group consisting of: $R^3$ and $R^7$ are a methyl group, and $R^4$, $R^5$ and $R^6$ are a hydrogen atom; $R^3$, $R^5$ and $R^7$ are a methyl group, and $R^4$ and $R^6$ are a hydrogen atom; $R^3$ is a methyl group, and $R^4$, $R^5$, $R^6$ and $R^7$ are a hydrogen atom; $R^3$ and $R^5$ are Y, and $R^4$, $R^6$ and $R^7$ are a hydrogen atom; $R^3$ is Y, and $R^4$, $R^5$, $R^6$ and $R^7$ are a hydrogen atom; $R^3$ is Y, and $R^4$, $R^5$ and $R^7$ are a hydrogen atom, and $R^6$ is a methyl group; $R^3$ and $R^7$ are a methyl group, and $R^4$ and $R^6$ are a hydrogen atom, and $R^5$ is Y; and $R^3$ is Y, and $R^4$ is X, and $R^5$ and $R^7$ are a hydrogen atom, and $R^6$ is a methyl group.

Then, a method for producing the heteroaromatic-containing compound according to the present invention will be described by way of one example.
The production route for producing the heteroaromatic-containing compound is not especially limited, and any production method can be employed. For example, a method of using, as raw materials, an aldehyde of an aromatic hydrocarbon group A in the above general formula (1) and a hydrogenated heterocyclic group including a heterocyclic compound in the above general formula (1) is desirable because not utilizing a special reaction. In this case, a hydrogenated heterocyclic group including a heterocyclic compound in the above general formula (1), or an organometal species prepared from a substituted compound capable of being converted to the organometal species, and an aldehyde of the aromatic compound are allowed to react to obtain an alcohol, which is then oxidized to produce the heteroaromatic-containing compound described above. At this time, in the case of using a raw material having an unstable substituent under the reaction condition described above, the substituent is desirably protected for the reaction. In the case of producing the heteroaromatic-containing compound described above by using a raw material having a hydroxyl group, the similar reaction is carried out after the hydroxyl group is protected, and after the hydroxyl group is deprotected, as many hydroxyl groups as necessary are (meth)acrylated.

The organometal species is not especially limited as long as being capable of nucleophilically reacting with an aldehyde, and is lithium species, magnesium species and the like. From thiophene indicated as a heterocyclic compound, lithium species can be prepared by allowing butyllithium, t-butyllithium or the like to act on thiophene. Magnesium species may be prepared by allowing magnesium, isopropylmagnesium bromide or the like to act on 2-bromothiophnes. The preparation condition of organometal species is not especially limited as long as being well-known ones, and the preparation is desirably carried out by using an etheric solvent such as dehydrated tetrahydropyran or diethyl ether. At this time, the preparation of lithium species is desirably carried out at a low temperature.

For the oxidation, any oxidation method can be utilized with particularly no limit as long as it is a well-known method. The oxidizing agent includes ozone, hydrogen peroxide, potassium permanganate, potassium chlorate, potassium dichromate, sodium bromate, a halogen, osmium tetroxide, manganese dioxide, DMSO, a Dess Martin reagent, peracetic acid, mCPBA, chromic acid, lead oxide, and TPAP, but is not limited thereto. However, in the case of utilizing peroxides, the oxidation of heteroatoms must be paid attention to.

A protecting group of a hydroxyl group is not especially limited as long as being suited to the reaction condition, and includes a methoxymethyl group, a tetrahydropyranyl group, and a silyl-based protecting group such as a trimethylsilyl group. Any of well-known methods may be used as the protection condition and the deprotection condition.

The (meth)acrylation reaction can be selected optionally. Representative methods thereof to be suitably used include a method in which a hydroxyl group is esterified by using a (meth)acrylic acid halide or (meth)acrylic anhydride, a transesterification using an ester of (meth)acrylic acid and a lower alcohol, and a direct esterification in which (meth)acrylic acid and the diol are dehydrated and condensed by using a dehydrating condensation agent such as N,N'-dicyclohexylcarbodiimide.

A polymerization inhibitor may be added, as required, to the heteroaromatic-containing compound containing a (meth)acrylate group according to the present invention so that the polymerization of the compound does not proceeds during reaction and during preservation. Examples of the polymerization inhibitor include hydroquinones such as p-benzoquinone, hydroquinone, hydroquinone monomethyl ether and 2,5-diphenyl-p-benzoquinone, N-oxy radicals such as a tetramethylpiperidinyl-N-oxy radical (TEMPO), substituted catechols such as t-butylcatechol, amines such as phenothiazine, diphenylamine and phenyl-β-naphthylamine, nitrosobenzene, picric acid, molecular oxygen, sulfur, and copper(II) chloride. Above all, hydroquinones, phenothiazine and N-oxy radicals can be used from the viewpoint of versatility and polymerization retardation, and hydroquinones can especially be used.

The amount of a polymerization inhibitor to be used is usually 10 ppm or more and can be 50 ppm or more for the lower limit, and usually 10,000 ppm or less and can be 1,000 ppm or less for the upper limit. The case of too small an amount thereof develops no effect or little effect as a polymerization inhibitor, and has a risk of progress of the polymerization during the reaction and during concentration in post-treatment steps; and the case of too large an amount thereof, for example, gives impurities in production of an optical material described later, and has a risk of giving adverse effects such as inhibition of polymerization reactivity, which are not desirable.

Then, the optical material according to the present invention will be described.
The optical material of the present invention comprises a composition containing the heteroaromatic-containing compound described above and a polymerization initiator, and as required, a photosensitizer and a resin.

The content of a heteroaromatic-containing compound contained in the optical material of the present invention is 1.0% by weight or more and 99% by weight or less, and can be 10% by weight or more and 80% by weight or less. Too low a content of the heteroaromatic-containing compound cannot give a desired θg, F characteristic; and too high a content of the heteroaromatic-containing compound does not progress crosslinking of a molded article to make a brittle molded article.

The polymerization initiator includes ones generating radical species and ones generating cation species by light irradiation, and ones generating radical species by heat, but is not limited thereto.

The polymerization initiator generating radical species by light irradiation includes 2-benzyl-2-dimethylamino-1-(4- morpholinophenyl)-1-butanone, 1-hydroxy-cyclohexyl-phenyl ketone, 2-hydroxy-2-methyl-1-phenyl-propane-1-one, bis(2,4,6-trimethylbenzoyl)-phenylphosphine oxide, 4-phenylbenzophenone, 4-phenoxybenzophenone, 4,4'-diphenylbenzophenone and 4,4'-diphenoxybenzophenone, but is not limited thereto.

The polymerization initiator generating cation species by light irradiation includes (4-methylphenyl)[4-(2-methylpropyl)phenyl]iodonium-hexafluorophosphate as a suitable polymerization initiator, but is not limited thereto.

The polymerization initiator generating radical species by heat includes azo compounds such as azobisisobutyronitrile (AIBN), and peroxides such as benzoyl peroxide, t-butyl peroxypivalate, t-butyl peroxyneohexanoate, t-hexyl peroxyneohexanoate, t-butyl peroxyneodecanoate, t-hexyl peroxyneodecanoate, cumyl peroxyneohexanoate and cumyl peroxyneodecanoate, but is not limited thereto.

For initiating polymerization by directing ultraviolet rays or the like as light, a well-known sensitizer or the like may be used. Representative sensitizers include benzophenone, 4,4-diethylaminobenzophenone, 1-hydroxycyclohexyl phenyl ketone, isoamyl p-dimethylaminobenzoate, methyl 4-dimethylaminobenzoate, benzoin, benzoin ethyl ether, benzoin isobutyl ether, benzoin isopropyl ether, 2,2-diethoxyacetophenone, methyl o-benzoylbenzoate, 2-hydroxy-2-methyl-1-phenylpropan-1-one and acylphosphine oxide.

The addition ratio of a photopolymerization initiator to a polymerizable resin component can suitably be selected according to the light irradiation amount, and further the additional heating temperature. The ratio can also be adjusted according to the target average molecular weight of a polymer to be obtained.

The addition amount of a photopolymerization initiator used in curing and molding of the optical material of the present invention can be in the range of 0.01% by weight or more and 10.00% by weight or less to a polymerizable component. The photopolymerization initiator can be used singly, or can be used in combination of two or more thereof, depending on the reactivity of a resin and the wavelength of light to be directed.

Utilizable resins are not especially limited, and examples thereof include (meth)acrylate compounds such as 1,3-adamantanediol dimethacrylate, 1,3-adamantanedimethanol dimethacrylate, tricyclodecanedimethanol diacrylate, pentaerythritol tetraacrylate, propoxylated neopentyl glycol diacrylate, dipropylene glycol diacrylate, ethoxylated bisphenol A dimethacrylate, tris(2-hydroxyethyl)isocyanurate triacrylate, 2-(2-ethoxyethoxy)ethyl acrylate, stearyl acrylate, tetrahydrofurfuryl acrylate, 2-phenoxyethyl acrylate, isodecyl acrylate, isobornyl acrylate, isobornyl methacrylate, 1,3-butylene glycol diacrylate, 1,4-butanediol diacrylate, diethylene glycol diacrylate, 1,6-hexanediol diacrylate, triethylene glycol diacrylate, tripropylene glycol diacrylate, dipropylene glycol diacrylate, triethylene glycol dimethacrylate, ethylene glycol dimethacrylate, tetraethylene glycol dimethacrylate, 1,4-butanediol dimethacrylate, diethylene glycol dimethacrylate, 1,6-hexanediol dimethacrylate, tripropylene glycol dimethacrylate, dipropylene glycol dimethacrylate, trimethylolpropane trimethacrylate, 9,9-bis[4-(2-acryloyloxyethoxy)phenyl]fluorene, 9,9-bis[4-(2-methacryloyloxyethoxy)phenyl]fluorene, 9,9-bis[4-(2-acryloyloxy)phenyl]fluorene, 9,9-bis[4-(2-methacryloyloxy)phenyl]fluorene, benzyl acrylate, benzyl methacrylate, butoxyethyl acrylate, butoxymethyl methacrylate, cyclohexyl acrylate, cyclohexyl methacrylate, 2-hydroxyethyl acrylate, 2-hydroxymethyl methacrylate, glycidyl acrylate, glycidyl methacrylate, phenoxyethyl acrylate, phenoxyethyl methacrylate, phenyl methacrylate, ethylene glycol diacrylate, ethylene glycol dimethacrylate, diethylene glycol diacrylate, diethylene glycol dimethacrylate, triethylene glycol diacrylate, triethylene glycol dimethacrylate, tetraethylene glycol diacrylate, tetraethylene glycol dimethacrylate, polyethylene glycol diacrylate, polyethylene glycol dimethacrylate, neopentyl glycol diacrylate, neopentyl glycol dimethacrylate, ethylene glycol bisglycidylacrylate, ethylene glycol bisglycidylmethacrylate, bisphenol A diacrylate, bisphenol A dimethacrylate, 2,2-bis(4-acryloxyethoxyphenyl)propane, 2,2-bis(4-methacryloxyethoxyphenyl)propane, 2,2-bis(4-acryloxydiethoxyphenyl)propane, 2,2-bis(4-methacryloxydiethoxyphenyl)propane, bisphenol F diacrylate, bisphenol F dimethacrylate, 1,1-bis(4-acryloxyethoxyphenyl)methane, 1,1-bis(4-methacryloxyethoxyphenyl)methane, 1,1-bis(4-acryloxydiethoxyphenyl)methane, 1,1-bis(4-methacryloxydiethoxyphenyl)methane, 1,1-bis(4-acryloxyethoxyphenyl) sulfone, 1,1-bis(4-methacryloxyethoxyphenyl) sulfone, 1,1-bis(4-acryloxydiethoxyphenyl) sulfone, 1,1-bis(4-methacryloxydiethoxyphenyl) sulfone, dimethyloltricyclodecane diacrylate, trimethylolpropane triacrylate, trimethylolpropane trimethacrylate, glycerol diacrylate, glycerol dimethacrylate, pentaerythritol triacrylate, pentaerythritol tetraacrylate, pentaerythritol tetramethacrylate, methyl thioacrylate, methyl thiomethacrylate, phenyl thioacrylate, benzyl thiomethacrylate, xylylenedithiol diacrylate, xylylenedithiol dimethacrylate, mercaptoethyl sulfide diacrylate and mercaptoethyl sulfide dimethacrylate, allyl compounds such as allyl glycidyl ether, diallyl phthalate, diallyl terephthalate, diallyl isophthalate, diallyl carbonate and diethylene glycol bisallylcarbonate, vinyl compounds such as styrene, chlorostyrene, methylstyrene, bromostyrene, dibromostyrene, divinylbenzene and 3,9-divinylspirobi(m-dioxane), and diisopropenylbenzene, but are not limited thereto.

The resins described above may be thermoplastic resins, and examples thereof include polyolefinic resins such as ethylene homopolymers, random or block copolymers of ethylene with one or two or more α-olefins of propylene, 1-butene, 1-pentene, 1-hexene, 4-methyl-1-pentene and the like, random or block copolymers of ethylene with one or two or more of vinyl acetate, acrylic acid, methacrylic acid, methyl acrylate and methyl methacrylate, propylene homopolymers, random or block copolymers of propylene with one or two or more α-olefins of 1-butene, 1-pentene, 1-hexene, 4-methyl-1-pentene and the like, excluding propylene, 1-butene homopolymers, ionomer resins, and mixtures of these polymers; hydrocarbon atom-based resins such as petroleum resins and terpene resins; polyesteric resins such as polyethylene terephthalate, polybutylene terephthalate, and polyethylene naphthalate; polyamide resins such as nylon 6, nylon 66, nylon 11, nylon 12, nylon 610, nylon 6/66, nylon 66/610 and nylon MXD; acrylic resins such as polymethyl methacrylate; styrene and acrylonitrile resins such as polystyrene, styrene-acrylonitrile copolymers, styrene-acrylonitrile-butadiene copolymers and polyacrylonitrile; polyvinyl alcoholic resins such as polyvinyl alcohol and ethylene-vinyl alcohol copolymers; polycarbonate resins; polyketone resins; polymethylene oxide resins; polysulfone resins; polyimide resins; and polyamideimide resins. These may be used singly or as a mixture of two or more thereof.

The content of the resin contained in the optical material of the present invention is 1.0% by weight or more and 99% by weight or less, and can be 20% by weight or more and 90% by weight or less in consideration of the θg, F characteristic of an optical material to be obtained and the brittleness of molded articles.

A method for forming a molded article of the optical material of the present invention involves, for example, in order to form a thin layer structure on a substrate made of a light transmissive material, installing a mold made of a metal material on a glass substrate, casting a fluid optical material or optical resin composition into between the both, and slightly pressing for mold-shaping. The optical material or optical resin composition is polymerized with this state being kept. Light irradiation used for such a polymerization reaction is carried out using light of a suitable wavelength, usually ultraviolet light or visible light corresponding to the mechanism causing the radical generation using a photopolymerization initiator. For example, the light irradiation is carried out uniformly to the raw material having been molded such as a monomer for preparing an optical material, through a light transmissive material utilized as the substrate, specifically, the glass substrate. The amount of light directed is suitably selected corresponding to the mechanism causing the radical generation utilizing a photopolymerization initiator, and corresponding to the content rate of the photopolymerization initiator contained.

Meanwhile, in fabrication of a molded article of an optical material by such a photopolymerization reaction, light to be directed can further be uniformly directed over the whole of a raw material such as a monomer having been molded. Therefore, in the light irradiation to be utilized, light of a wavelength can further be selected so that the light irradiation can be carried out uniformly through a light transmissive material utilized as a substrate, for example, the glass substrate. At this time, making thin the total thickness of a molded article of an optical material formed on a substrate of a light transmissive material is more suitable for the present invention.

A molded article can be similarly fabricated by a thermal polymerization method. In this case, making the temperature of the whole more uniform is desirable, and making thin the total thickness of a molded article of a polymerizable composition formed on a substrate of a light transmissive material is more suitable for the present invention. In the case where the total thickness of a molded article to be formed of an optical material is made thick, the irradiation amount, the irradiation intensity, a light source and the like need to be selected taking into more consideration the film thickness, the absorption by resin components and the absorption by microparticle components.

Meanwhile, a process of forming a molded article of a mixed composition with a thermoplastic resin described above is not especially limited, but in order to obtain a molded article excellent in characteristics such as low birefringence, mechanical strength, size precision and the like, melt molding can especially be used. The melt molding includes press molding, extrusion and injection molding, and injection molding can be used from the viewpoint of moldability and productivity. The molding condition in the molding step is suitably selected depending on usage purposes and molding methods, and the temperature of a resin composition in injection molding can be in the range of 150° C. to 400° C., can further be in the range of 200° C. to 350° C., and can especially be in the range of 200° C. to 330° C. Molding in the above-mentioned temperature range can impart a reasonable fluidity to a resin at the time of molding to prevent molded articles from generating sink marks and strains, prevent silver streaks from being generated due to thermal decomposition of the resin, and further prevent effectively molded articles from turning yellow.

Molded articles obtained by molding the optical material of the present invention by the above-mentioned molding method can be used as optical elements. Examples of the optical element include camera lenses.

Example 1

Hereinafter, the present invention will be described in more detail, but is not limited to the following Examples unless departing from the gist of the present invention. Analysis of synthesized products was carried out using a JNM-ECA400 NMR, made by JEOL Ltd.

First, a synthesis method of 2-(4-bromo-3,5-dimethylphenoxy)tetrahydropyran (Synthesis Example 1) will be described. 0.01 g of pyridinium p-toluenesulfonate was added to a chloroform solution of 50 g of 4-bromo-3,5-dimethylphenol and 35 g of 3,4-dihydro-2H-pyran, and stirred. After the confirmation of the degree of reaction progress by TLC, the reaction was terminated with triethylamine, and an organic phase was washed with water and saturated brine in order. After the obtained organic phase was dried with anhydrous magnesium sulfate, the organic phase was concentrated and purified by column chromatography to obtain 70 g (yield: 98%) of 2-(4-bromo-3,5-dimethylphenoxy)tetrahydropyran as a colorless liquid.

150 ml of a tetrahydrofuran solution of 16.7 g of 2-(4-bromo-3,5-dimethylphenoxy)tetrahydropyran synthesized in (Synthesis Example 1) described above was cooled to −78° C., and 23 ml (2.6 M) of n-butyllithium was slowly dropped thereto. After the mixture was stirred at the same temperature for 2 hours, 10 g of 5-phenylthiophene-2-carboaldehyde was added thereto, and stirred for 12 hours while the temperature was being raised to room temperature. After the confirmation of the degree of reaction progress by TLC (thin-layer chromatography), the reaction was terminated with an ammonium chloride aqueous solution, and an organic phase was extracted with ethyl acetate.

After the obtained organic phase was dried with anhydrous magnesium sulfate, the organic phase was concentrated and purified by column chromatography. Then, 15 g of manganese dioxide was added to a chloroform solution of the obtained product, and the mixture was stirred at room temperature for 24 hours. After the confirmation of the degree of reaction progress by TLC, and after the manganese dioxide was filtered, the solvent was concentrated to obtain a concentrate.

1 ml of 6N hydrochloric acid was added to 50 ml of a tetrahydrofuran solution of the concentrate, and the mixture was stirred at room temperature for 12 hours. After the confirmation of the degree of reaction progress by TLC, the reaction was terminated with a sodium hydrogencarbonate aqueous solution, and an organic phase was extracted with ethyl acetate. After the obtained organic phase was dried with anhydrous magnesium sulfate, the organic phase was concentrated, and 13.1 g (yield: 84%) of Product 1 shown below was obtained as a white crystal by recrystallization. The structure of Product 1 was confirmed by 1HNMR. The optical characteristics, transmittance and stability of Product 1 are shown in Table 1.

Formula 8

Product 1

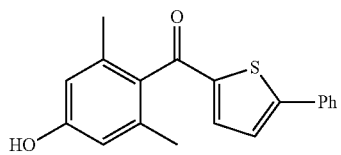

$^1$H-NMR (CDCl3; TMS): δ 2.19 (s, 6H), 5.41 (s, 1H), 6.55 (s, 2H), 7.26-7.44 (m, 5H), 7.67 (d, 2H)

Example 2

150 ml of a chloroform solution of 13 g of the compound (Product 1) synthesized in Example 1 was cooled to 0° C., and after 6.5 g of methacrylic acid chloride and 12 g of triethylamine were dropped thereto in order, the mixture was stirred for 2 hours while the temperature was being raised to 25° C. After the confirmation of the degree of reaction progress by TLC, the reaction was terminated with a sodium hydrogencarbonate aqueous solution, and after an organic phase was extracted with ethyl acetate, the obtained organic phase was washed with a 0.5N sodium hydroxide aqueous solution.

After the obtained organic phase was dried with anhydrous magnesium sulfate, the organic phase was concentrated, and purified by column chromatography to obtain 11 g (yield: 69%) of Product 2 shown below as a white crystal. The structure of Product 2 was confirmed by 1HNMR. The optical characteristics, transmittance and stability of Product 2 are shown in Table 1.

Formula 9

Product 2

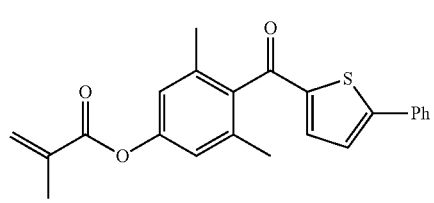

$^{1}$H-NMR (CDCl3; TMS): δ 2.07 (s, 3H), 2.25 (s, 6H), 5.78 (s, 1H), 6.36 (s, 1H), 6.88 (s, 2H), 7.26-7.45 (m, 5H), 7.67 (d, 2H)

Example 3

In Example 3, 10 g (yield: 66%) of Product 3 was obtained by altering 6.5 g of methacrylic acid chloride in the method described in Example 2 to 6.0 g of acrylic acid chloride. The structure of Product 3 was confirmed by 1HNMR. The optical characteristics, transmittance and stability of Product 3 are shown in Table 1.

Formula 10

Product 3

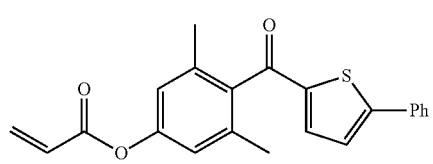

$^{1}$H-NMR (CDCl3; TMS): δ 2.07 (s, 3H), 2.25 (s, 6H), 5.78 (d, 1H), 6.36 (d, 1H), 6.40 (dd, 1H), 6.88 (s, 2H), 7.26-7.45 (m, 5H), 7.67 (d, 2H)

Example 4

0.2 g of the compound (Product 1) synthesized in Example 1 was added to 10 ml of a N,N-dimethylformamide solution of 0.03 g of sodium hydride (55%) at 0° C., and the mixture was stirred at the same temperature for 1 hour. 0.14 g of 2-(2-bromoethoxy)tetrahydro-2H-pyran was added thereto, and the mixture was stirred for 12 hours while the temperature was being raised to 25° C. After the confirmation of the degree of reaction progress by TLC, the reaction was terminated with an ammonium chloride aqueous solution, and an organic phase was extracted with ethyl acetate. After the obtained organic phase was concentrated, the organic phase was made a tetrahydrofuran solution (10 ml), and 0.5 ml of a 6N hydrochloric acid aqueous solution was added to the solution, and stirred at 25° C. for 12 hours. After the confirmation of the degree of reaction progress by TLC, the reaction was terminated with a sodium hydrogencarbonate aqueous solution, and an organic phase was extracted with ethyl acetate. The obtained organic phase was concentrated, and purified by column chromatography to obtain an intermediate compound.

Then, 0.21 g (yield: 71%) of Product 4 was obtained similarly by the method described in Example 2, except for altering 13 g of the compound (Product 1) synthesized in Example 1 to 0.32 g of the intermediate compound, 6.5 g of methacrylic acid chloride to 0.14 g of methacrylic acid chloride, and 12 g of triethylamine to 0.18 g of triethylamine. The structure of Product 4 was confirmed by 1HNMR. The optical characteristics, transmittance and stability of Product 4 are shown in Table 1.

Formula 11

Product 4

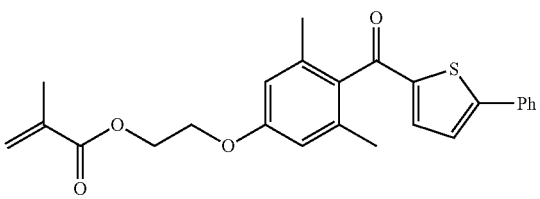

$^{1}$H-NMR (CDCl3; TMS): δ 2.21 (s, 6H), 3.81-3.92 (m, 2H), 4.12-4.20 (m, 2H) 5.64 (d, 1H), 6.12 (d, 1H), 6.83 (s, 2H), 7.26-7.45 (m, 5H), 7.66 (d, 2H)

Example 5

0.2 g of the compound (Product 1) synthesized in Example 1 was added to 10 ml of a tetrahydrofuran solution of 0.03 g of sodium hydride (55%) at 0° C., and the mixture was stirred at the same temperature for 1 hour. 0.14 g of 2-(2-bromoethoxy)tetrahydro-2H-pyran was added thereto, and the mixture was stirred for 12 hours while the temperature was being raised to 25° C. After the confirmation of the degree of reaction progress by TLC, the reaction was terminated with an ammonium chloride aqueous solution, and an organic phase was extracted with ethyl acetate. After the obtained organic phase was concentrated, the organic phase was made a tetrahydrofuran solution (10 ml), and 0.5 ml of a 6N hydrochloric acid aqueous solution was added to the solution, and stirred at 25° C. for 12 hours. After the confirmation of the degree of reaction progress by TLC, the reaction was terminated with a sodium hydrogencarbonate aqueous solution, and an organic phase was extracted with ethyl acetate. The obtained organic phase was concentrated, and purified by column chromatography to obtain an intermediate compound.

Then, 0.15 g (yield: 65%) of Product 5 was obtained similarly by the method described in Example 2, except for altering 13 g of the compound (Product 1) synthesized in Example 1 to 0.32 g of the intermediate compound, 6.5 g of methacrylic acid chloride to 0.14 g of methacrylic acid chloride, and 12 g of triethylamine to 0.18 g of triethylamine. The structure of Product 5 was confirmed by 1HNMR. The optical characteristics, transmittance and stability of Product 5 are shown in Table 1.

Formula 12

Product 5

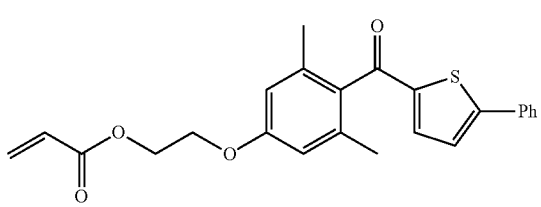

¹H-NMR (CDCl3; TMS): δ 2.20 (s, 6H), 3.80-3.90 (m, 2H), 4.10-4.18 (m, 2H) 5.78 (d, 1H), 6.36 (d, 1H), 6.40 (dd, 1H), 6.78 (s, 2H), 7.26-7.45 (m, 5H), 7.67 (d, 2H)

Example 6

25 ml of a tetrahydrofuran solution of 1.0 g of phenylthiophene was cooled to −78° C., and 2.6 ml (2.6 M) of n-butyllithium was slowly dropped thereto, and stirred at the same temperature for 2 hours. Thereafter, 0.65 g of 2,6-dimethylbenzaldehyde was added thereto, and stirred for 12 hours while the temperature was being slowly raised to 25° C. After the confirmation of the degree of reaction progress by TLC, the reaction was terminated with an ammonium chloride aqueous solution, and an organic phase was extracted with ethyl acetate.

After the obtained organic phase was dried with anhydrous magnesium sulfate, the organic phase was concentrated and purified by column chromatography. 5 g of manganese dioxide was added to 30 ml of a chloroform solution of the obtained intermediate compound, and the mixture was stirred at 25° C. for 12 hours. After the confirmation of the degree of reaction progress by TLC, the manganese dioxide was filtered, and 0.57 g (yield: 40%) of Product 6 shown below was obtained as a white crystal by recrystallization. The structure of Product 6 was confirmed by 1HNMR. The optical characteristics, transmittance and stability of Product 6 are shown in Table 1.

Formula 13

Product 6

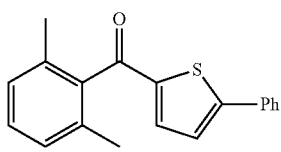

¹H-NMR (CDCl3; TMS): δ 2.24 (s, 6H), 7.08 (d, 2H), 7.22-7.29 (m, 3H), 7.37-7.42 (m, 3H), 7.66 (d, 2H)

Example 7

In Example 7, 0.69 g (yield: 41%) of Product 7 was obtained as a white crystal by altering 0.65 g of 2,6-dimethylbenzaldehyde in the method described in Example 6 to 0.72 g of ortho-tolualdehyde. The structure of Product 7 was confirmed by 1HNMR. The optical characteristics, transmittance and stability of Product 7 are shown in Table 1.

Formula 14

Product 7

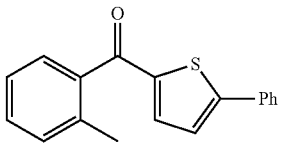

¹H-NMR (CDCl3; TMS): δ 2.41 (s, 3H), 7.25-7.47 (m, 9H), 7.66-7.68 (m, 2H)

Example 8

In Example 8, 0.71 g (yield: 43%) of Product 8 was obtained as a white crystal by altering 0.65 g of 2,6-dimethylbenzaldehyde in the method described in Example 6 to 0.78 g of 2,4,6-trimethylbenzaldehyde. The structure of Product 8 was confirmed by ¹HNMR. The optical characteristics, transmittance and stability of Product 8 are shown in Table 1.

Formula 15

Product 8

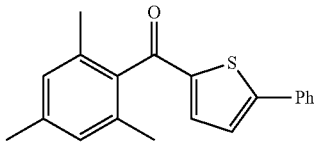

¹H-NMR (CDCl3; TMS): δ 2.24 (s, 6H), 2.31 (s, 3H), 7.08 (d, 2H), 7.22-7.29 (m, 3H), 7.37-7.42 (m, 3H), 7.66 (d, 2H)

Example 9

In Example 9, 0.75 g (yield: 52%) of Product 9 was obtained as a white crystal by the method described in Example 6, by altering 0.65 g of 2,6-dimethylbenzaldehyde to 0.82 g of 2-methyl-1-naphthylaldehyde. The structure of Product 9 was confirmed by 1HNMR. The optical characteristics, transmittance and stability of Product 9 are shown in Table 1.

Formula 16

Product 9

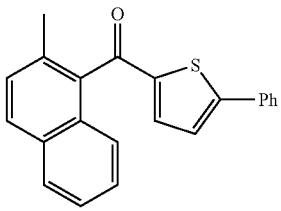

¹H-NMR (CDCl3; TMS): δ 2.27 (s, 3H), 7.15-7.29 (m, 5H), 7.31-7.41 (m, 4H) 7.51-7.60 (m, 4H)

Example 10

First, a synthesis method (Synthesis Example 2) of 2-methoxymethoxybenzaldehyde will be described. 3 g of salicylaldehyde was slowly added to an N,N-dimethylformamide solution (50 ml) of 1.2 g of sodium hydride (55%) at 0° C., and stirred at the same temperature for 1 hour. Then, 2.9 g of chloromethyl methyl ether was added thereto, and after the confirmation of the degree of reaction progress by TLC, the reaction was terminated with an ammonium chloride aqueous solution. After an organic phase was extracted with ethyl acetate, the organic phase was dried with anhydrous magnesium sulfate. A crude product obtained by concentrating the organic phase was purified by column chromatography to obtain 3.9 g (yield: 96%) of 2-methoxymethoxybenzaldehyde.

In Example 10, 0.65 g of 2,6-dimethybenzaldehyde in the method described in Example 6 was altered to 1.2 g of 2-methoxymethoxybenzaldehyde synthesized in (Synthesis Example 2) described above to obtain an intermediate compound. 1 ml of a 6N hydrochloric acid was added to a tetrahydrofuran solution (30 ml) of the obtained intermediate compound, and the mixture was stirred at 25° C. for 12 hours. After the confirmation of the degree of reaction progress by TLC, the reaction was terminated with a sodium hydrogencarbonate aqueous solution, and an organic phase was extracted with ethyl acetate.

After the obtained organic phase was dried with anhydrous magnesium sulfate, the organic phase was concentrated, and 1.4 g (yield: 84%) of Product 10 shown below was obtained as a white crystal by recrystallization. The structure of Product 10 was confirmed by 1HNMR. The optical characteristics, transmittance and stability of Product 10 are shown in Table 1.

Formula 17

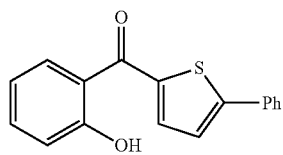

Product 10

$^1$H-NMR (CDCl3; TMS): δ 6.97 (d, 1H), 7.08 (d, 1H), 7.38-7.54 (m, 5H), 7.69-7.74 (m, 3H), 7.99 (d, 1H), 11.60 (s, 1H)

Example 11

2.5 g (yield: 96%) of Product 11 was obtained similarly by the method described in Example 2, except for altering 13 g of the compound (Product 1) synthesized in Example 1 to 2.0 g of the compound (Product 10) synthesized in Example 10, 6.5 g of methacrylic acid chloride to 0.9 g of methacrylic acid chloride, 12 g of triethylamine to 1.5 g of triethylamine, and 150 ml of the chloroform solution to 20 ml of the chloroform solution. The structure of Product 11 was confirmed by 1HNMR. The optical characteristics, transmittance and stability of Product 11 are shown in Table 1.

Formula 18

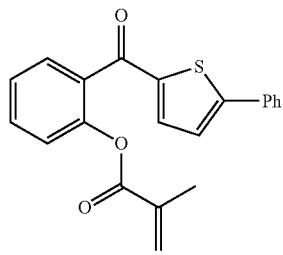

Product 11

$^1$H-NMR (CDCl3; TMS): δ 1.83 (s, 3H), 5.41 (s, 1H), 6.12 (s, 1H) 7.03-7.19 (m, 6H), 7.28-7.31 (m, 2H), 7.44-7.48 (m, 3H)

Example 12

First, a synthesis method (Synthesis Example 3) of 2-methoxymethoxy-5-methylbenzaldehyde will be described. 3.3 g (yield: 90%) of 2-methoxymethoxy-5-methylbenzaldehyde was obtained similarly by the method described in Synthesis Example 2, except for altering 3 g of salicylaldehyde to 2.8 g of 5-methylsalicylaldehyde.

In Example 12, 0.65 g of 2,6-dimethybenzaldehyde in the method described in Example 6 was altered to 1.3 g of 2-methoxymethoxy-5-methylbenzaldehyde synthesized in (Synthesis Example 3) described above. 1 ml of a 6N hydrochloric acid was added to a tetrahydrofuran solution (30 ml) of the obtained intermediate compound, and the mixture was stirred at 25° C. for 12 hours. After the confirmation of the degree of reaction progress by TLC, the reaction was terminated with a sodium hydrogencarbonate aqueous solution, and an organic phase was extracted with ethyl acetate. After the obtained organic phase was dried with anhydrous magnesium sulfate, the organic phase was concentrated, and 1.5 g (yield: 84%) of Product 12 shown below was obtained as a white crystal by recrystallization. The structure of Product 12 was confirmed by $^1$HNMR. The optical characteristics, transmittance and stability of Product 12 are shown in Table 1.

Formula 19

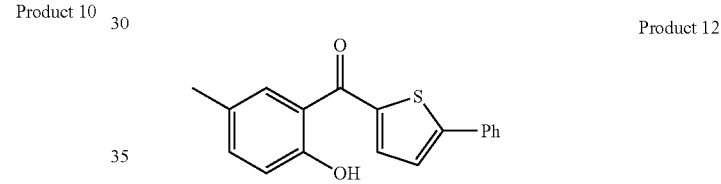

Product 12

$^1$H-NMR (CDCl3; TMS): δ 2.41 (s, 3H), 7.17 (d, 1H), 7.25-7.45 (m, 7H), 7.66 (d, 2H), 11.58 (s, 1H)

Example 13

1.0 g (yield: 77%) of Product 13 was obtained similarly by the method described in Example 2, except for altering 13 g of the compound (Product 1) synthesized in Example 1 to 1.0 g of the compound (Product 12) synthesized in Example 12, 6.5 g of methacrylic acid chloride to 0.5 g of methacrylic acid chloride, 12 g of triethylamine to 0.7 g of triethylamine, and 150 ml of the chloroform solution to 20 ml of the chloroform solution. The structure of Product 13 was confirmed by 1HNMR. The optical characteristics, transmittance and stability of Product 13 are shown in Table 1.

Formula 20

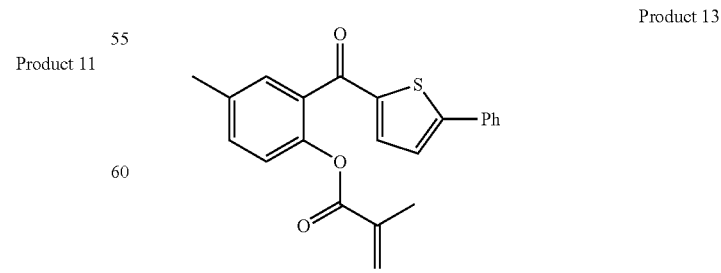

Product 13

$^1$H-NMR (CDCl3; TMS): δ 1.90 (s, 3H), 2.41 (s, 3H), 5.60 (s, 1H), 6.14 (s, 1H), 7.17 (d, 1H), 7.25-7.45 (m, 7H), 7.66 (d, 2H)

Example 14

First, a synthesis method of 2,4-bis(methoxymethoxy)benzaldehyde will be described. 5.9 g (90%) of 2,4-bis(methoxymethoxy)benzaldehyde was obtained similarly by the method described in Synthesis Example 2, except for altering 1.2 g of sodium hydride (55%) to 3 g of sodium hydride (55%), 3 g of salicylaldehyde to 4 g of 2,4-dihydroxybenzaldehyde, and 2.9 g of chloromethyl methyl ether to 6.5 g of chloromethyl methyl ether.

In Example 14, 0.65 g of 2,6-dimethybenzaldehyde in the method described in Example 6 was altered to 1.7 g of 2,4-bis(methoxymethoxy)benzaldehyde synthesized in (Synthesis Example 4) described above. 1 ml of a 6N hydrochloric acid was added to a tetrahydrofuran solution (30 ml) of the obtained intermediate compound, and the mixture was stirred at 25° C. for 12 hours. After the confirmation of the degree of reaction progress by TLC, the reaction was terminated with a sodium hydrogencarbonate aqueous solution, and an organic phase was extracted with ethyl acetate. After the obtained organic phase was dried with anhydrous magnesium sulfate, the organic phase was concentrated, and 1.6 g (yield: 87%) of Product 14 shown below was obtained as a white crystal by recrystallization. The structure of Product 14 was confirmed by 1HNMR. The optical characteristics, transmittance and stability of Product 14 are shown in Table 1.

Formula 21

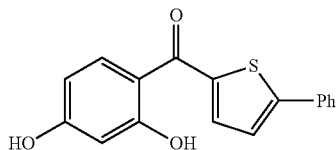

Product 14

$^1$H-NMR (CDCl3; TMS): δ 5.35 (s, 1H), 7.18 (d, 2H), 7.26-7.49 (m, 5H), 7.65-7.68 (m, 3H), 11.58 (s, 1H)

Example 15

1.3 g (yield: 85%) of Product 15 was obtained similarly by the method described in Example 2, except for altering 13 g of the compound (Product 1) synthesized in Example 1 to 1.0 g of the compound (Product 14) synthesized in Example 14, 6.5 g of methacrylic acid chloride to 0.85 g of methacrylic acid chloride, 12 g of triethylamine to 1.4 g of triethylamine, and 150 ml of the chloroform solution to 20 ml of the chloroform solution. The structure of Product 15 was confirmed by $^1$HNMR. The optical characteristics, transmittance and stability of Product 15 are shown in Table 1.

Formula 22

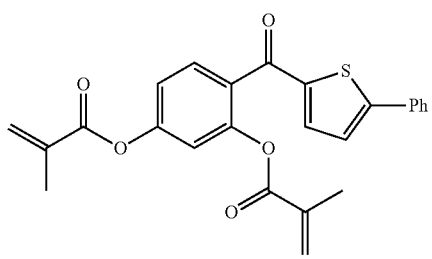

Product 15

$^1$H-NMR (CDCl3; TMS): δ 1.91 (s, 3H), 2.07 (s, 3H), 5.64 (s, 1H), 5.81 (s, 1H), 6.17 (s, 1H), 6.38 (s, 1H), 7.18 (d, 2H), 7.26-7.49 (m, 5H), 7.65-7.68 (m, 3H)

Example 16

40 ml of a tetrahydrofuran solution of 3.0 g of phenylthiophene was cooled to −78° C., and 8.6 ml (2.6 M) of n-butyllithium was slowly dropped thereto, and stirred at the same temperature for 2 hours. Thereafter, 0.85 g of 2-hydroxy-5-methylisophthalaldehyde was added thereto, and stirred for 12 hours while the temperature was being slowly raised to 25° C. After the confirmation of the degree of reaction progress by TLC, the reaction was terminated with an ammonium chloride aqueous solution, and an organic phase was extracted with ethyl acetate.

After the obtained organic phase was dried with anhydrous magnesium sulfate, the organic phase was concentrated and purified by column chromatography. 10 g of manganese dioxide was added to 30 ml of a chloroform solution of the obtained intermediate compound, and the mixture was stirred at 25° C. for 12 hours. After the confirmation of the degree of reaction progress by TLC, the manganese dioxide was filtered, and 1.1 g (yield: 44%) of Product 16 shown below was obtained as a white crystal by recrystallization. The structure of Product 16 was confirmed by $^1$HNMR. The optical characteristics, transmittance and stability of Product 16 are shown in Table 1.

Formula 23

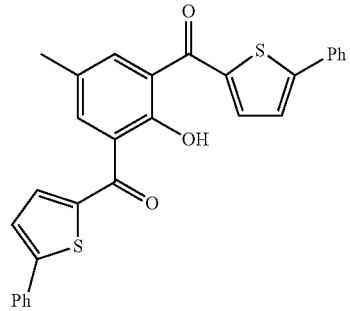

Product 16

$^1$H-NMR (CDCl3; TMS): δ 2.41 (s, 3H), 7.37-7.46 (m, 8H), 7.66-7.74 (m, 8H), 11.78 (s, 1H)

Comparative Example 1

In Comparative Example 1, 0.94 g (yield: 90%) of Comparative Product 1 was obtained by altering 1.0 g of phenylthiophene in the method described in Example 6 to 1.0 g of 2-bromothiophene. The structure of Comparative Product 1 was confirmed by 1HNMR. The optical characteristics, transmittance and stability of Comparative Product 1 are shown in Table 1.

Formula 24

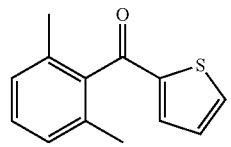

Comparative Product 1

$^1$H-NMR (CDCl3; TMS): δ 2.20 (s, 6H), 7.06-7.10 (m, 3H), 7.21-7.26 (m, 1H), 7.33 (d, 1H), 7.73 (d, 1H)

Comparative Example 2

In Comparative Example 2, 0.85 g (yield: 66%) of Comparative Product 2 was obtained by altering 1.0 g of phenylthiophene in the method described in Example 6 to 0.8 g of benzothiophene. The structure of Comparative Product 2 was confirmed by 1HNMR. The optical characteristics, transmittance and stability of Comparative Product 2 are shown in Table 1.

Formula 25

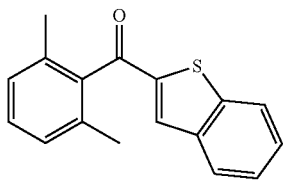

Comparative Product 2

¹H-NMR (CDCl3; TMS): δ 2.23 (s, 6H), 7.11 (d, 2H), 7.28 (t, 1H), 7.39 (t, 1H), 7.46-7.52 (m, 2H), 7.79 (d, 1H), 7.90 (d, 1H)

Comparative Example 3

1.2 ml of a tetrahydrofuran solution of 0.25 g of magnesium was cooled to 0° C., and 5.0 ml of a tetrahydrofuran solution of 1.0 g of 2-bromoindene was slowly dropped thereto. After the dropping, the mixture was stirred at the same temperature for 1 hour, and 0.57 g of 2,6-dimethylbenzaldehyde was added thereto, and stirred for 12 hours while the temperature was being raised to 25° C. After the confirmation of the degree of reaction progress by TLC, the reaction was terminated with an ammonium chloride aqueous solution, and an organic phase was extracted with ethyl acetate.

After the obtained organic phase was dried with anhydrous magnesium sulfate, the organic phase was concentrated and purified by column chromatography. Then, 5 g of manganese dioxide was added to 30 ml of a chloroform solution of the obtained intermediate compound, and the mixture was stirred at 25° C. for 12 hours. After the confirmation of the degree of reaction progress by TLC, the manganese dioxide was filtered, and 0.42 g (yield: 40%) of Comparative Product 3 shown below was obtained by recrystallization. The structure of Comparative Product 3 was confirmed by 1HNMR. The optical characteristics, transmittance and stability of Comparative Product 3 are shown in Table 1.

Formula 26

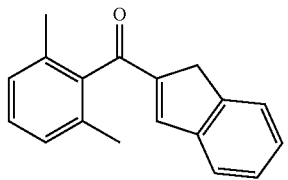

Comparative Product 3

¹H-NMR (CDCl3; TMS): δ 2.21 (s, 6H), 3.85 (s, 2H), 7.07 (d, 2H), 7.20-7.26 (m, 2H), 7.33-7.41 (m, 2H), 7.47 (d, 1H), 7.58 (d, 1H)

(Evaluations)

The refractive index was measured using an Abbe's refractometer (Kalnew Optical Industrial Co., Ltd.). The transmittance was measured by molding a film of 50 μm in optical path length and using a spectrophotometer U-4000 (product name), made by Hitachi High-Technologies Corp. The transmittance was indicated as a transmittance at a wavelength of 430 nm.

With respect to the stability, the case where there was no deterioration in preservation in the air at 25° C. for 2 weeks was denoted as ○; and the case where there occurred deterioration therein was denoted as x. Provided that with respect to a product having a polymerizable substituent, the determination was carried out in the state of containing a small amount (1,000 ppm or less) of a polymerization inhibitor.

A product exhibiting optical characteristics within the B range in FIG. 1 and a transmittance at a wavelength of 430 nm of 90% or more was comprehensively evaluated as ○; and a product other than the former product was comprehensively evaluated as x.

TABLE 1

| | | nd | vd | θg, F | Transmittance | Stability | Comprehensive Evaluation |
|---|---|---|---|---|---|---|---|
| Example 1 | Product 1 | 1.66 | 13.31 | 0.847 | 96 | ○ | ○ |
| Example 2 | Product 2 | 1.64 | 14.79 | 0.843 | 93 | ○ | ○ |
| Example 3 | Product 3 | 1.64 | 14.63 | 0.845 | 94 | ○ | ○ |
| Example 4 | Product 4 | 1.59 | 15.01 | 0.821 | 95 | ○ | ○ |
| Example 5 | Product 5 | 1.59 | 14.96 | 0.824 | 94 | ○ | ○ |
| Example 6 | Product 6 | 1.67 | 13.22 | 0.850 | 93 | ○ | ○ |
| Example 7 | Product 7 | 1.69 | 12.43 | 0.869 | 92 | ○ | ○ |
| Example 8 | Product 8 | 1.66 | 13.68 | 0.843 | 94 | ○ | ○ |
| Example 9 | Product 9 | 1.71 | 12.03 | 0.876 | 93 | ○ | ○ |
| Example 10 | Product 10 | 1.67 | 12.96 | 0.861 | 93 | ○ | ○ |
| Example 11 | Product 11 | 1.65 | 13.95 | 0.864 | 94 | ○ | ○ |
| Example 12 | Product 12 | 1.66 | 13.14 | 0.881 | 92 | ○ | ○ |
| Example 13 | Product 13 | 1.65 | 13.65 | 0.873 | 93 | ○ | ○ |
| Example 14 | Product 14 | 1.65 | 13.89 | 0.864 | 94 | ○ | ○ |
| Example 15 | Product 15 | 1.63 | 14.60 | 0.866 | 95 | ○ | ○ |
| Example 16 | Product 16 | 1.76 | 11.78 | 0.893 | 93 | ○ | ○ |
| Comparative Example 1 | Comparative Product 1 | 1.60 | 22.50 | 0.658 | 97 | ○ | x |
| Comparative Example 2 | Comparative Product 2 | 1.65 | 17.04 | 0.720 | 95 | ○ | x |
| Comparative Example 3 | Comparative Product 3 | 1.62 | 17.30 | 0.698 | 94 | ○ | x |

The present invention can provide a heteroaromatic-containing compound having a high dispersion characteristic of refractive index (Abbe number (vd)), a high secondary dispersion characteristic (high θg, F characteristic), and a high characteristic of the chromatic aberration correction function, and an optical material and an optical element using the same.

The present invention can also provide an optical material having characteristics within the range B in FIG. 1. Use of an optical element molded of the optical material can efficiently remove the chromatic aberration. Therefore, an optical system can be more reduced in weight and size. A high θg, F characteristic used hereinafter refers to within the range B in FIG. 1.

This application claims the benefit of Japanese Patent Application No. 2009-298642, filed Dec. 28, 2009, which is hereby incorporated by reference herein in its entirety.

The invention claimed is:

1. A heteroaromatic-containing compound, represented by general formula (1):

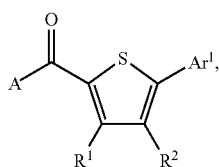

general formula (1)

wherein $R^1$ and $R^2$ are each independently a hydrogen atom or a methyl group; $Ar^1$ is an optionally substituted aryl group and A is an aromatic hydrocarbon group represented by general formula (3):

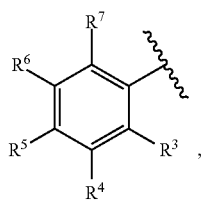

general formula (3)

wherein $R^3$ to $R^7$ are each independently X, Y, a hydrogen atom, an alkyl group having 1 to 4 carbon atoms, or an optionally substituted aryl group provided that at least one of $R^3$ to $R^7$ is Y; X is

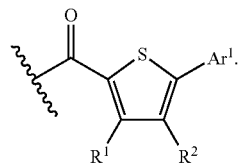

and Y is a group represented by general formula (4):

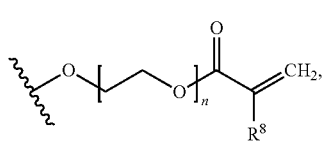

general formula (4)

wherein $R^8$ is a hydrogen atom or a methyl group; and n is 0 or 1.

2. The heteroaromatic-containing compound according to claim 1, wherein the $R^1$ and $R^2$ are a hydrogen atom; and $Ar^1$ is a phenyl group.

3. A heteroaromatic-containing compound, represented by general formula (1):

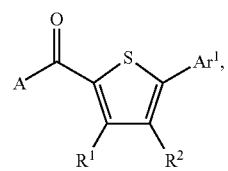

general formula (1)

wherein $R^1$ and $R^2$ are each independently a hydrogen atom or a methyl group; $Ar^1$ is an optionally substituted aryl group and A is an aromatic hydrocarbon group represented by general formula (2):

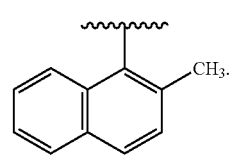

general formula (2)

4. The hetero aromatic-containing compound according to claim 1, wherein $R^3$ to $R^7$ in the general formula (3) are one combination selected from the combination group consisting of: $R^3$ and $R^5$ are Y, and $R^4$, $R^6$ and $R^7$ are a hydrogen atom; $R^3$ and $R^4$ are Y, and $R^5$, $R^6$ and $R^7$ are a hydrogen atom; $R^3$ is Y, and $R^4$, $R^5$, $R^6$ and $R^7$ are a hydrogen atom; $R^3$ is Y, and $R^4$, $R^5$ and $R^7$ are a hydrogen atom, and $R^6$ is a methyl group; $R^3$ and $R^7$ are a methyl group, and $R^4$ and $R^6$ are a hydrogen atom, and $R^5$ is Y; $R^3$ is Y, and $R^4$ and $R^6$ are a tert-butyl group, and $R^5$ and $R^7$ are a hydrogen atom; $R^3$, $R^5$ and $R^7$ are Y, and $R^4$ and $R^6$ are a hydrogen atom; $R^3$, $R^4$ and $R^5$ are Y, and $R^6$ and $R^7$ are a hydrogen atom; $R^3$ is Y, and $R^4$ is a methyl group, and $R^5$, $R^6$ and $R^7$ are a hydrogen atom; $R^3$ is Y, and $R^4$ is X, and $R^5$, $R^6$ and $R^7$ are a hydrogen atom; and $R^3$ is Y, and $R^4$ is X, and $R^5$ and $R^7$ are a hydrogen atom, and $R^6$ is a methyl group.

5. An optical material, comprising a heteroaromatic-containing compound according to claim 1.

6. An optical lens comprising a resin on a glass, wherein the resin comprises the optical material according to claim 5.

7. An optical material, comprising a heteroaromatic-containing compound according to claim 3.

8. An optical lens comprising a resin on a glass, wherein the resin comprises the optical material according to claim 7.

* * * * *